United States Patent [19]

Ellingboe

[11] Patent Number: 5,451,583

[45] Date of Patent: Sep. 19, 1995

[54] SUBSTITUTED BENZIMIDAZOLES AND QUINAZOLINES AS ANTIHYPERTENSIVES

[75] Inventor: John W. Ellingboe, Princeton, N.J.

[73] Assignee: American Home Products Corporation, Madison, N.J.

[21] Appl. No.: 353,428

[22] Filed: Dec. 9, 1994

Related U.S. Application Data

[60] Continuation of Ser. No. 126,282, Sep. 24, 1993, abandoned, which is a division of Ser. No. 975,198, Nov. 12, 1992, Pat. No. 5,283,242, which is a continuation-in-part of Ser. No. 782,845, Oct. 24, 1991, abandoned.

[51] Int. Cl.⁶ .................. A61K 31/415; C07D 235/06
[52] U.S. Cl. .................... 514/254; 514/318; 514/322; 514/333; 514/338; 514/383; 514/394; 544/370; 546/194; 546/199; 546/271; 548/310.1; 548/250; 548/254
[58] Field of Search .............. 544/370; 546/194, 199, 546/271; 548/310.1, 250, 254; 514/254, 318, 322, 338, 333, 383, 394

[56] References Cited

U.S. PATENT DOCUMENTS

| | | | |
|---|---|---|---|
| 4,808,715 | 2/1989 | Boyle et al. | 544/235 |
| 4,880,804 | 11/1989 | Carini | 514/239.5 |
| 5,039,814 | 8/1991 | Shuman | 548/250 |
| 5,187,168 | 2/1993 | Primeau | 514/259 |
| 5,210,092 | 5/1993 | Oku et al. | 514/338 |
| 5,215,994 | 6/1993 | Oku et al. | 514/226 |
| 5,234,936 | 8/1993 | Primeau | 514/259 |
| 5,283,242 | 2/1994 | Ellingboe | 514/186 |

FOREIGN PATENT DOCUMENTS 411766 6/1990 European Pat. Off. .
426021A 5/1991 European Pat. Off. .

OTHER PUBLICATIONS

Chem. Abst. 115:232250c (1991).
Chem. Abst. 115: 159142n (1991).
Chem. Abst. 115:71602b (1991).
Chem. Abst. 114:228914j (1991).
Chem. Abst. 114:164233b (1991).
Chiu, A., Euro Jour. Pharma: 157, 13–21 (1988).

Primary Examiner—Mukund J. Shah
Assistant Examiner—Matthew V. Grumbling
Attorney, Agent, or Firm—Arthur G. Seifert

[57] ABSTRACT

There are disclosed compounds of the formula

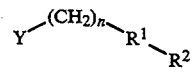

wherein $R^1$ and $R^2$ are defined in the specification;
n is 1 to 3;
Y is

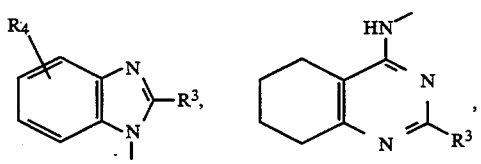

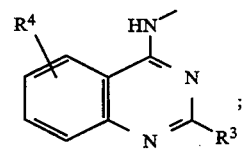

wherein $R^3$ is hydrogen, perfluoro alkyl of 1–6 carbon atoms, trifluoromethylalkyl of 1–6 carbon atoms, or alkyl of 1–6 carbon atoms; and $R^4$ is hydrogen or alkyl of 1–6 carbon atoms;
with the proviso that when $R^1$ is

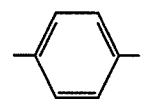

then $R^2$ cannot be (Abstract continued on next page.)

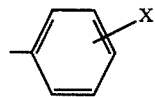
wherein X is as defined above;
and the pharmaceutically acceptable salts thereof, which by virtue of their ability to antagonize angiotensin II are useful for the treatment of hypertension and congestive heart-failure.
14 Claims, No Drawings

SUBSTITUTED BENZIMIDAZOLES AND QUINAZOLINES AS ANTIHYPERTENSIVES

This is a continuation of U.S. Ser. No. 08/126,282, filed Sep. 24, 1993, now abandoned which is a divisional application of application U.S. Ser. No. 07/975,198, filed Nov. 12, 1992, now U.S. Pat. No. 5,283,242 which is in turn a continuation-in-part application of application U.S. Ser. No. 07/782,845, filed Oct. 24, 1991, now abandoned.

BACKGROUND OF THE INVENTION

This invention relates to substituted benzimidazoles and quinazolines which are useful for the treatment of hypertension and congestive heart failure.

These compounds achieve their hemodynamic effects by antagonizing the effects of angiotensin II; the active component of the renin angiotensin system. Angiotensinogen is converted to angiotensin I by the action of the enzyme renin. Angiotensin II (A II) is formed by angiotensin converting enzyme (ACE) acting on angiotensin I. A II is a powerful vasoconstrictor and is implicated as the cause of high blood pressure in a number of species including man. A II elicits these vasopressor responses by acting at specific receptor sites. The compounds described in this invention compete with A II for these receptor sites, thus antagonizing the vasopressor effects of A II.

E. E. Allen et al. disclose N-substituted oxopyrimidines in EP 0419048 A. E. E. Allen et al. describe 4-oxoquinazolines in EP 0411766 A. D. A. Roberts et al. describe quinoline ethers in EP 0412848 A. D. J. Carini et al. in U.S. Pat. No. 4,880,804 describe N-substituted benzimidazoles. P. Chakravarty et al. disclose similar imidazole structures in EP 0401030 A where the phenyl aromatic ring is replaced by a seven membered heterocycle. Azabenzimidazoles are described by P. Herold et al. in EP 0415886 A. D. J. Carini et al. disclose N-substituted imidazoles in EP 0253310, EP 0324377, and U.S. Pat. No. 4,916,129. D. J. Carini et al. disclose N-substituted pyrazoles, pyrroles and triazoles in EP 0323841. Similar pyrazole derivatives are disclosed by T. Naka et al. in EP 0411507 A and additional triazoles are described by L. L. Chang et al. in EP 0412594 A. All of the above are claimed as A II antagonists.

The compounds of this invention differ from the above mentioned prior art in that they contain a bicyclic heterocycle such as a N-substituted benzimidazole, 4-aminosubstituted quinazoline, or 4-amino substituted tetrahydroquinazoline ring, in which the substituent on the heterocycle is not the biphenyltetrazole described in the above patents.

DESCRIPTION OF THE INVENTION

This invention relates to substituted benzimidazoles and quinazolines of the general formula I:

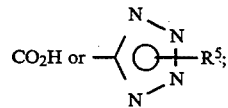

wherein
$R^1$ is

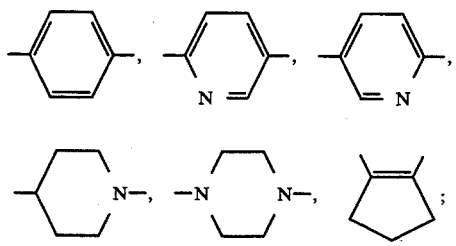

$R^2$ is

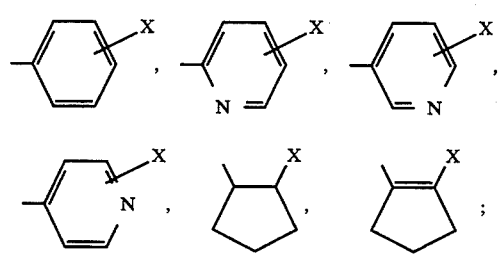

wherein X is

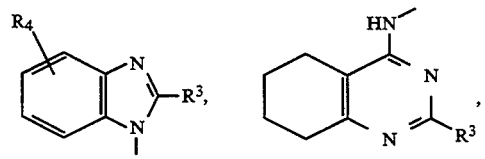

wherein $R^5$ is hydrogen, alkyl of 1–6 carbon atoms, benzyl, triphenylmethyl, or Sn(alkyl of 1–6 carbon atoms)$_3$;
n is 1 to 3;
Y is

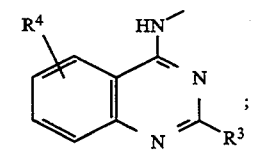

wherein $R^3$ is hydrogen, perfluoro alkyl of 1–6 carbon atoms, trifluoromethylalkyl of 1–6 carbon atoms, or alkyl of 1–6 carbon atoms; and $R^4$ is hydrogen or alkyl of 1–6 carbon atoms;
with the proviso that when $R^1$ is

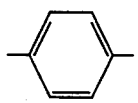

then $R^2$ cannot be

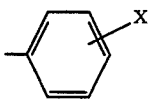

wherein X is as defined above;
and the pharmaceutically acceptable salts thereof.

A preferred aspect of the present invention is represented by general formula I:

$$Y-(CH_2)_n-R^1-R^2 \quad I$$

wherein
$R^1$ is

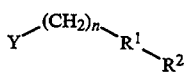

$R^2$ is

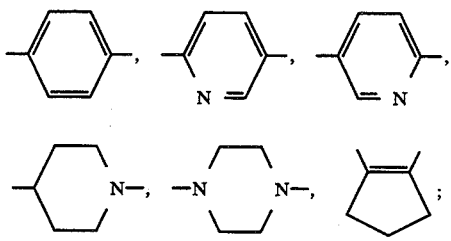

wherein X is $CO_2H$ or 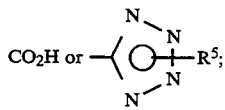

wherein $R^5$ is hydrogen, alkyl of 1–6 carbon atoms, benzyl, triphenylmethyl, or Sn(alkyl of 1–6 carbon atoms)$_3$;
n is 1 to 3;
Y is

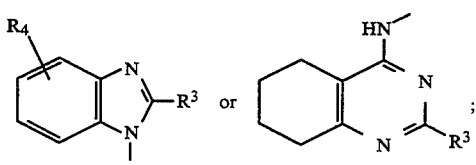

wherein $R^3$ is hydrogen, perfluoro alkyl of 1–6 carbon atoms, trifluoromethylalkyl of 1–6 carbon atoms, or alkyl of 1–6 carbon atoms; and $R^4$ is hydrogen or alkyl of 1–6 carbon atoms;

with the proviso that when $R^1$ is

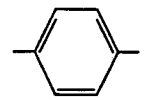

then $R^2$ cannot be

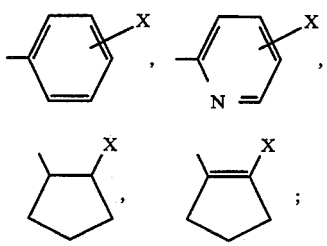

wherein X is as defined above;
and the pharmaceutically acceptable salts thereof.

Specifically preferred compounds are:

2-propyl-1-[[2-[2-(1H-tetrazol-5-yl)phenyl]-1-cyclopentenyl]methyl]-1H-benzimidazole and the pharmaceutically acceptable salts thereof;

2-propyl-1-[[2-[3-(1H-tetrazol-5-yl)phenyl]-1-cyclopentenyl]methyl]-1H-benzimidazole and the pharmaceutically acceptable salts thereof;

2-[4-[(2-propyl-1H-benzimidazol-1-yl)methyl]phenyl]-1-cyclopentene-1-carboxylic acid and the pharmaceutically acceptable salts thereof;

2-[4-[(2-propyl-1H-benzimidazol-1-yl)methyl]phenyl]-cyclopentane-1-carboxylic acid and the pharmaceutically acceptable salts thereof;

2-propyl-1-[2-[4-[2-(1H-tetrazol-5-yl)phenyl]-1-piperazinyl]ethyl]-1H-benzimidazole and the pharmaceutically acceptable salts thereof;

2-propyl-1-[2-[1-[2-(1H-tetrazol-5-yl)phenyl]-4-piperidinyl]ethyl]-1H-benzimidazole and the pharmaceutically acceptable salts thereof;

2-propyl-1-[[2-[2-(1H-tetrazol-5-yl)phenyl]-5-pyridinyl]methyl]-1H-benzimidazole and the pharmaceutically acceptable salts thereof;

4-methyl-2-propyl-1-[[2-[2-(1H-tetrazol-5-yl)phenyl]-5-pyridinyl]methyl]-1H-benzimidazole and the pharmaceutically acceptable salts thereof;

5,6,7,8-tetrahydro-N-[[2'-(1H-tetrazol-5-yl)phenyl]-5-pyridinyl]methyl]-2-(trifluoromethyl)-4-quinazolinamine and the pharmaceutically acceptable salts thereof;

2-[4-[(2-propyl-1H-benzimidazol-1-yl)methyl]phenyl]-3-pyridinecarboxylic acid and the pharmaceutically acceptable salts thereof.

Process

The compounds of the present invention are prepared according to the general sequences of reactions outlined below:

Scheme I

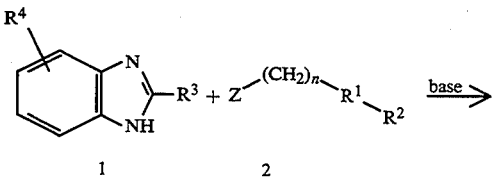

1)

-continued
Scheme I

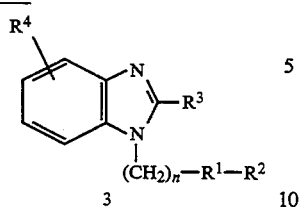
3

2)

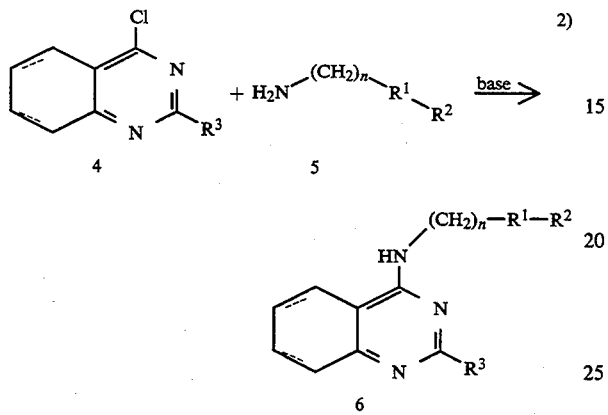

wherein $R^1$, $R^2$, $R^3$, $R^4$, and n are as defined above; the X substituent on $R^2$ is a carboxylic acid, a carboxylic acid alkyl ester, a nitrile, or a tetrazole; and Z is chloro, bromo, iodo, or alkylsulfonate.

As illustrated in Scheme I, part 1), a benzimidazole 1 is alkylated with the compound of formula 2 in the presence of a base such as NaH or LDA in an aprotic solvent such as THF or DMF at temperatures ranging from −78° C. to 100° C. to yield the alkylated benzimidazole of formula 3. As illustrated in Scheme I, part 2), a quinazoline or tetrahydroquinazoline 4 is treated with the amine of formula 5 in the presence of an organic base such as triethylamine or an inorganic base such as sodium carbonate in a polar solvent such as EtOH, DMF, or DMSO at temperatures ranging from ambient to 150° C. to yield the 4-aminoquinazoline or tetrahydroquinazoline 6.

In the case where the X substituent on $R^2$ of compounds 3 and 6 is a carboxylic acid ester, basic or acidic hydrolysis gives the target compounds 3 and 6 where the X substituent on $R^2$ is a carboxylic acid. In the case where the X substituent on $R^2$ of compounds 3 and 6 is a nitrile, treatment with an azide reagent such as ammonium azide or a trialkyltin azide gives the target compounds 3 and 6 where the X substituent on $R^2$ is a tetrazole.

Some examples of the preparation of the compounds 2 and 5 of Scheme I are illustrated in Scheme II below:

Scheme II

1)

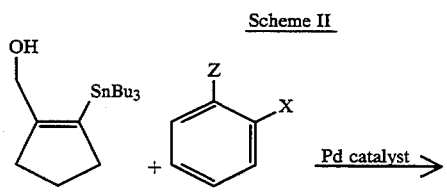

-continued
Scheme II

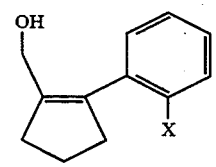
9

2)

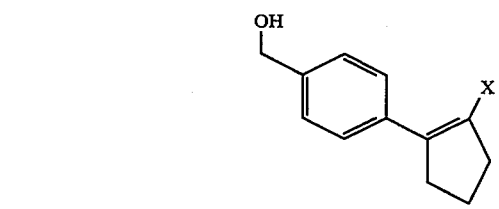
12

3)

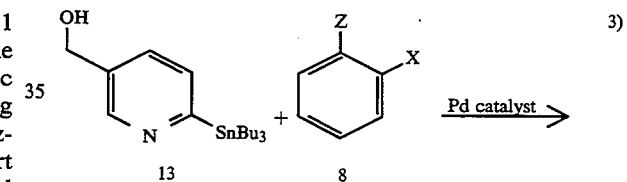

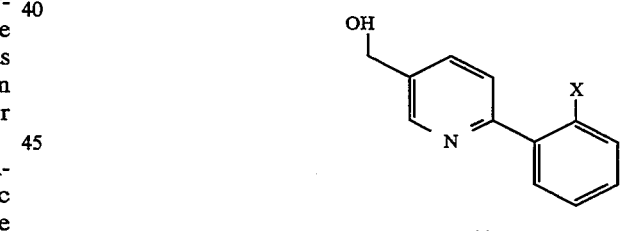
14

4)

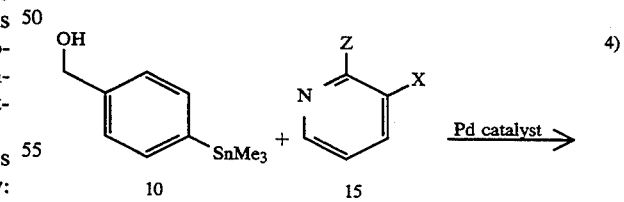

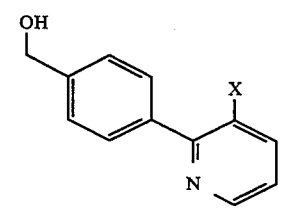
16

-continued
Scheme II

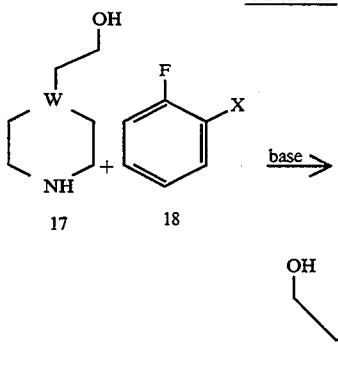

wherein the X substituent on $R^2$ is a carboxylic acid, a carboxylic acid alkyl ester, a nitrile, or a tetrazole; Z is bromo, iodo, trifluoromethanesulfonate, or alkylsulfonate; and W is $CH_2$ or N.

As shown in parts 1) to 4) of Scheme II, an aryl (10), pyridyl (13), or vinyl (7) stannane is reacted with an aryl (8), pyridyl (15), or vinyl (11) compound in the presence of a palladium catalyst in an organic solvent such as THF, toluene, or DMF at temperatures ranging from ambient to 150° C. to give the coupled products 9, 12, 14, and 16. Shown in part 5) of Scheme II is the reaction of the cyclic amino compound 17 with the aryl fluoride 18 in the presence of an inorganic base such as sodium carbonate in a polar solvent such as DMF or DMSO at temperatures ranging from 50°–150° C. to yield the compound of formula 19.

The hydroxy groups of compounds 9, 12, 14, 16, and 19 can be converted to the Z group (chloro, bromo, iodo, or alkylsulfonate) of compounds 2 and 5 in Scheme I with standard halogenating reagents or alkylsulfonyl chlorides.

The compounds of this invention may also form salts with inorganic or organic bases. Any pharmaceutically acceptable salts of these compounds are within the scope of this invention. These salts may be, but are not limited to, ammonium salts, alkali metal salts such as sodium and potassium, alkaline earth metal salts such as calcium, dicyclohexylamine salts, TRIS salts, and salts of amino acids. These compounds may also be converted to N-oxides by treatment with hydrogen peroxide by conventional means.

The present invention also provides a pharmaceutical composition which comprises a compound of this invention and a pharmaceutically acceptable carder. In particular, the present invention provides an anti-hypertensive pharmaceutical composition which comprises an antihypertensive effective amount of a compound of this invention and a pharmaceutically acceptable carrier.

The compositions are preferably adapted for oral administration. However, they may be adapted for other modes of administration, for example parenteral administration for patients suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 1 to 50 mg. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day. The compounds may also be administered in a parenteral dosing form.

The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics, $\beta$-blocking agents or ACE inhibitors.

The present invention further provides a compound of the invention for use as an active therapeutic substance. Compounds described in this invention are of particular use in the treatment of hypertension. They can also be used for the treatment of congestive heart-failure.

The present invention further provides a method of treating hypertension in mammals including man, which comprises administering to the afflicted mammal an antihypertensive effective amount of a compound or a pharmaceutical composition of the invention.

Pharmacology

The high affinity of the compounds for the angiotensin II receptor was established using a rat adrenal receptor binding assay, measuring the displacement of radiolabeled angiotensin II from the receptor, described as follows: Anesthetize male Sprague-Dawley rats (300–400 g body weight) with $CO_2$ and sacrifice by cervical dislocation. Dissect adrenal glands and keep in ice-cold sucrose buffer (0.2M sucrose, 1 mM EDTA, 10 mM Trizma base, pH=7.2). Remove medulla by squashing. Mince the cortex, rinse and homogenize in a chilled ground glass tissue grinder with 15 mL sucrose buffer. Centrifuge at $3000 \times g$ for 10 min. (Sorvall RCSC centrifuge, SS34 rotor 6200 rpm). Decant supernatant through gauze. Centrifuge combined supernatant at $12000 \times g$ for 13 min. (Beckman ultracentrifuge, 80Ti rotor, 13000 rpm). Centrifuge the supernatant from the previous step at $102000 \times g$ for 60 min. (Beckman ultracentrifuge, 80Ti rotor, 38200 rpm). All steps are carried out at 4° C. Resuspend the pellet in 0.5 mL assay buffer (50 mM Tris HCI, 5 mM $MgCl_2$, 0.2% BSA (protease-free), pH=7.4, 25° C.). Store on ice. Determine membrane protein by Lowry or Bradford assay with BSA as standard. The binding assay is performed in triplicate, in $12 \times 75$ mm plastic test tubes or in a 96-well plate (final volume of 0.25 mL). Add 140 $\mu$L assay buffer. Add 10 $\mu$L cold A II (to give final concentrations of $10^{-10}$–$10^{-7}$ M for standard curve and $10^{-4}$M for nonspecific binding), compounds (e.g., for final concentrations of 25 and 100 $\mu$M or 1 $\mu$M, 10 nM and 100 nM) in 50% DMSO, or 50% DMSO as a control. Add 50 $\mu$L membrane suspension (e.g., 10 $\mu$g protein). Preincubate for 30 min at 25° C. Add 50 $\mu$L $^{125}$I-A II which has been prepared as shown below (final concentration=1 nM). Incubate for 35 min at 25° C. Stop the incubation by adding 1 mL ice-cold buffer (assay buffer without BSA). Filter with GF/C filters on cell harvester (filters are presoaked in the assay buffer containing 1% polyethyleneimine). Rinse assay tubes $3\times$ with 5 mL cold buffer (assay buffer without BSA). Cut and deposit the filter discs into test tubes and count on gamma counter for 1 min. Adjust the specific activity of $^{125}$I-A II purchased from New England Nuclear to 500 $\mu$Ci/nmole by adding cold A II in water. Calculate the quantities of hot A II and the cold A II needed and make the dilution. Aliquot, seal tight, and store frozen until needed. Calculate the concentration of the total A II (hot+cold) after dilution. On the day of assay, thaw the frozen aliquot and adjust the volume to give a concentration of 5 pmole/mL (or 0.25 pmole/50 µL) with assay buffer (+protease-free BSA). For final concentration of 1 nM $^{125}$I-A II in the assay, add 50 µL (or 0.25 pmole) per test tube to a final volume of 250 µL. The results of these binding assays are reported as the inhibitory concentration of the test compound necessary to achieve fifty percent displacement of radiolabeled angiotensin II from its receptor (IC$_{50}$), or the percent displacement of binding of A II at its receptor at $10^{-8}$M concentration of test compound (% I). All the examples cited in this invention displayed significant inhibition of A II binding in this assay. Typically these compounds displayed an IC$_{50}$ in this assay of less than or equal to 200 µM as set forth below in the Table below.

TABLE

| Inhibition of $^{125}$I Angiotensin II Binding | |
|---|---|
| Example | IC$_{50}$ |
| 1 | 200 µM |
| 2 | 73 µM |
| 3 | 20 µM |
| 4 | 25 µM |
| 5 | 43 µM |
| 6 | 30 µM |
| 7 | 24 µM |
| 8 | 15 µM |
| 9 | 4.5 µM |
| 10 | 200 µM |

In accordance with their ability to antagonize angiotensin II, the compounds of this invention show antihypertensive action in the following A II-infused rat model. Rats are anesthetized with Dial-Urethane (0.60 mL/kg, ip) and the trachea cannulated with PE 240. Either one femoral artery and both femoral veins or the carotid artery and the corresponding jugular vein are cannulated with PE 50. If the jugular vein is cannulated, two cannulas are placed in the one vein. The initial portion of the duodenum (just distal to the stomach) is cannulated with PE 50 via a small midline incision. Arterial pressure and heart rate are measured from the arterial cannula. Ten to 15 min are allowed following surgery for stabilization of arterial pressure. Ganglion blockade is then produced by intravenous administration of mecamylamine at 3 mg/kg (1 mL/kg of a 3 mg/mL solution). Ganglion blockade causes a fall in arterial pressure of about 50 mmHg. Mecamylamine is given every 90 min throughout the remainder of the experiment. An A II infusion is then begun into the other venous cannula at 0.25 µg/kg/min (at 9.6 gL/min). The A II infusion returns arterial pressure to or slightly above the control level. Once arterial pressure has stabilized with the A II infusion, baseline values for mean arterial pressure (MAP) and heart rate are taken. The test compound, suspended in methyl cellulose, is then administered via the duodenal cannula at 0.1, 3 or, 30 mg/kg in a volume of 1 mL/kg. Mean arterial pressure and heart rate values are tabulated at 15, 30, 60, 90, 120, 150, 180, 210, and 240 min after administration of the test compound. For example, the product of Example 9 administered at 3 mg/kg id lowered the A II dependent blood pressure by an average of 70% four hours post-administration.

As illustrated above the compounds of this invention are effective A II antagonists and therefore are useful for treating hypertension. They are also of value in the management of acute and chronic congestive heart failure, primary and secondary pulmonary hyperaldosteronism, secondary hyperaldosteronism, primary and secondary pulmonary hypertension, hypertension associated with oral contraceptive use, vascular disorders such as migraine, Raynaud's disease, luminal hyperplasia and the atherosclerotic process, renal diseases or renal complications of other diseases or therapies such as proteinuria, glomerulonephritis, glomerular sclerosis, scleroderma, diabetic nephropathy, end stage renal disease, renal transplant therapy and others. These compounds will also be useful in the treatment of left ventricular dysfunction, diabetic retinopathy, Alzheimers disease, in the enhancement of cognition, in treatment of elevated intraoccular pressure, and in the enhancement of retinal blood flow. These compounds will also be useful as antidepressants and anxiolytics and in the prevention or treatment of restenosis following angioplasty. The application of the compounds of this invention for these and similar disorders will be apparent to those skilled in the art.

Specific procedures are described in the following examples. These examples are given to illustrate the invention and should not be construed as limiting the invention set forth in the appended claims.

EXAMPLES

EXAMPLE 1

2-Propyl-1-[[2-[2-(1H-tetrazol-5-yl)phenyl]-1-cyclopentenyl]methyl]1H-benzimidazole Step 1) [2-(Tri-n-butylstannyl)-1-cyclopentenyl]methanol To a cooled (−75° C.) solution of methyl [2-(tri-n-butylstannyl)-cyclopentene]carboxylate (4.8 g, 0.0116 mol) (prepared according to the procedure of Piers et al. Tetrahedron Lett. 1984,25, 3155) in THF (12 mL) was added diisobutylaluminum hydride (1M in THF; 25.4 mL, 0.0254 mol) over 10 min. The mixture was warmed to room temperature and stirred for 2 h, cooled to 0° C., and NaF (4.3 g, 0.102 mol) was added. Water and ether (100 mL) were added and the mixture was stirred at room temperature for 30 min. The solid was removed by filtration and washed with chloroform. The tiltrate was concentrated to give 4.3 g (96%) of product as a colorless oil.

$^1$H NMR (CDCl$_3$) δ 0.87 (m, 15H), 1.29 (m, 6H), 1.44 (m, 6H), 1.85 (m, 2H), 2.44 (m, 4H), 4.17 (d, J=5.0 Hz, 2H).

Step 2) 2-[(2-Hydroxymethyl)-1-cyclopentenyl]benzonitrile

To a stirred solution of 2-iodobenzonitrile (0.95 g, 4.13 mmol) and [2-(tri-n-butylstannyl)-1-cyclopentenyl]methanol (1.60 g, 4.13 mmol) in DMF (5 mL) was added bis(acetonitrile)palladium dichloride (54 mg, 0.21 mmol). After 24 h, 20% aqueous KF (40 mL) was added and the mixture was stirred for 1 h. EtOAc (20 mL) was added and the mixture was filtered. The filtrate layers were separated and the aqueous phase was extracted with EtOAc. The combined organic phases were washed with brine, 10% aqueous NH$_4$OH, brine, dried, and concentrated. Purification by flash chromatography (20% EtOAc/hexane) gave 615 mg (75%) of product as an oil.

$^1$H NMR (CDCl$_3$) δ 1.09 (m, 2H), 2.66 (t, J=7.2 Hz, 2H), 2.75 (t, J=7.2 Hz, 2H), 4.08 (s, 2H), 7.31 (m, 2H), 7.52 (m, 1H), 7.62 (d, J=8.2 Hz, 1H).

Step 3) 2-[(2-Chloromethyl)-1-cyclopentenyl]benzonitrile

To a stirred solution of 2-[(2-hydroxymethyl)-1-cyclopentenyl]benzonitrile (979 mg, 4.91 mmol) in DMF (5 mL) was added LiCl (271 mg, 6.39 mmol). After the LiCl dissolved (about 5 min), 2,6-lutidine (684 mg, 6.39 mol) was added and the mixture was cooled to 0° C. Methanesulfonyl chloride (732 mg, 6.39 mmol) was added, the cooling bath was removed, and stirring was continued for 17 h. Water was added and the mixture was extracted with ether. The combined extracts were washed with brine, dried, and concentrated to give 1.02 g (95%) of product as an oil.

$^1$H NMR (CDCl$_3$) δ 2.05 (m, 2H), 2.71 (t, J=7.5 Hz, 2H), 2.84 (t, J=7.6 Hz, 2H) 4.03 (s, 2H), 7.35 (m, 2H), 7.58 (m, 1H), 7.85 (d, J=7.8 Hz, 1H).

Step 4) 1-[1-[[(2-Cyanophenyl)-1-cyclopenten-2-yl]methyl]-2-propyl-1H-benzimidazole To a cooled (0° C.), stirred solution of 2-propyl-1H-benzimidazole (826 mg, 5.15 mmol) in DMF (5 mL) was added NaH (60% dispersion in mineral oil; 210 mg, 5.15 mmol). After 1 h, a solution of 2-[(2-chloromethyl)cyclopenten-1-yl]benzonitrile (1.02 g, 4.69 mmol) in DMF (4 mL) was added. The resultant mixture was stirred at room temperature for 20 h, cooled (0° C.), and diluted with water (50 mL). The mixture was extracted with EtOAc, and the combined extracts were washed with brine, dried, and concentrated. Purification by flash chromatography (30–50% EtOAc/hexane) gave 1.47 g (92%) of product as an off-white solid, mp 91°–95° C.

$^1$H NMR (CDCl$_3$) δ 0.95 (t, J=7.3 Hz, 3H), 1.80 (m, 2H), 1.95 (t, J=7.2 Hz, 2H 2.27 (t, J=7.0 Hz, 2H), 2.68 (m, 2H), 2.81 (t, J=7.3 Hz, 2H), 4.76 (s, 2H), 7.11 (m, 1H), 7.18 (m, 2H), 7.34 (d, J=7.8 Hz, 1H), 7.42 (m, 1H), 7.61 (d, J=7.8 Hz, 1H), 7.70 (m, 2H).

Step 5) 2-Propyl-1-[[2-[2-(1H-tetrazol-5-yl)phenyl]-1-cyclopentenyl]methyl]-1H-benzimidazole A mixture of 1-[1-[[(2-cyanophenyl)-cyclopenten]-2-yl]methyl]-2-propyl-1H-benzimidazole (1.44 g, 4.22 mmol), tri-n-butyltin chloride (1.51 g, 4.64 mmol), sodium azide (0.30 g, 4.64 mmol), and xylenes (15 mL) was heated under reflux for 48 h. 1N HCl (4.7 mL) and EtOAc (50 mL) were added and the layers were separated. The organic phase was washed with brine, stirred with 20% aqueous KF (50 mL) for 30 min, and filtered. The filtrate layers were separated, and the organic phase was dried and concentrated to give a brown oil. Purification by flash chromatography (5% MeOH/CHCl$_3$) and recrystallization from EtOH gave 459 mg (28%) of product as a beige solid, mp 186°–187° C.

$^1$H NMR (DMSO-d$_6$) δ 0.81 (t, J=7.3 Hz, 3H), 1.63 (m, 2H), 1.73 (m, 2H), 2.02 (t, J=7.3 Hz, 2H), 2.51 (m, 4H), 4.53 (s, 2H), 7.10 (m, 2H), 7.25 (m, 1H), 7.47 (m, 2H), 7.56 (m, 1H), 7.64 (m, 1H), 7.82 (dd, J=7.7, 1.2 Hz, 1H).

Anal. calcd for C$_{23}$H$_{24}$N$_6$: C, 71.85; H, 6.29; N, 21.86 Found: C, 71.66; H, 6.60; N, 21.60.

EXAMPLE 2

2-Propyl-1-[[2-[3-(1H-tetrazol-5-yl)phenyl]-1-cyclopentenyl]methyl]1H-benzimidazole The title compound was prepared from 3-iodobenzonitrile, by the procedure described in Example 1. The product was obtained as a white solid, mp 116°–119° C.

$^1$H NMR (DMSO-d$_6$) δ 0.80 (t, J=7.3 Hz, 3H), 1.64 (m, 2H), 1.80 (m, 2H), 2.10 (t, J=6.7 Hz, 2H), 2.54 (t, J=7.5 Hz, 2H), 2.82 (m, 2H), 5.10 (s, 2H), 7.11 (m, 2H), 7.27 (m, 1H), 7.51 (m, 1H), 7.59 (d, J=7.8 Hz, 1H), 7.67 (m, 1H), 8.01 (m, 2H).

Anal. calcd for C$_{23}$H$_{24}$N$_6$.0.5H$_2$O: C, 70.21; H, 6.40; N, 21.36 Found: C, 70.41; H, 6.40; N, 21.18.

EXAMPLE 3

2-[4-[(2-Propyl-1H-benzimidazol-1-yl)methyl]phenyl]-1-cyclopentene-1-carboxylic Acid Step 1) 4-(Trimethylstannyl)benzyl Alcohol A mixture of 4-bromobenzyl alcohol (4.5 g, 0.024 mol), hexamethyldistannane (9.5 g, 0.029 mol), (PPh$_3$)$_4$Pd (0.56 g, 4.8 mmol), and toluene (55 mL) was heated under reflux for 17 h. The mixture was concentrated, triturated with hexane, and the tiltrate was concentrated. Purification by flash chromatography (10% EtOAc/hexane) gave 1.65 g (25%) of product as an oil.

$^1$H NMR (CDCl$_3$) δ 0.27 (s, 9H), 4.66 (s, 2H), 7.33 (d, J=8.1 Hz, 2H), 7.49 (d, J=8.1 Hz, 2H).

Step 2) Methyl [2-[(4-Hydroxymethyl)phenyl]-1-cyclopentene]-1-carboxylate

To a cooled (10° C.), stirred solution of (2-carboxymethyl)-1-cyclopentenyl trifluoromethanesulfonate (Piers et al. Tetrahedron Lett. 1984,25, 3155) (1.10 g, 4.02 mmol), LiCl (0.34 g, 8.04 mmol), and bis(acetonitrile)-palladium dichloride (52 mg, 0.20 mmol) in DMF (8 mL) was added a solution of 4-(trimethylstannyl)benzyl alcohol (1.09 g, 4.02 mmol) in DMF (2 mL). After 2 h, EtOAc (50 mL) was added and the mixture was washed with brine, dried, and concentrated. Purification by flash chromatography (25% EtOAc/hexane) gave 864 mg (92%) of product as a colorless oil.

$^1$H NMR (CDCl$_3$) δ 1.97 (m, 2H), 2.81 (m, 4H), 3.61 (s, 3H), 4.67 (s, 2H), 7.31 (s, 4H).

Step 3) Methyl [2-[(4-Chloromethyl)phenyl]-1-cyclopentene]-1-carboxylate

To a cooled (0° C.), stirred solution of methyl [2-[(4-hydroxymethyl)phenyl]-1-cyclopentene]-1-carboxylate (1.05 g, 4.52 mmol), LiCl (250 mg, 5.88 mmol), and 2,6-lutidine (630 mg, 5.88 mmol) in DMF (5 mL) was added methanesulfonyl chloride (670 mg, 5.88 mmol). The cooling bath was removed and stirring was continued for 3 days. Water was added and the mixture was extracted with EtOAc. The combined extracts were washed with brine, saturated aqueous CuSO$_4$, brine, dried, and concentrated to give 1.13 g (100%) of product as a brown oil.

$^1$H NMR (CDCl$_3$) δ 1.99 (m, 2H), 2.84 (m, 4H), 3.63 (s, 3H), 4.59 (s, 2H), 7.33 (m, 4H).

Step 4) Methyl 2-[4-[(2-Propyl-1H-benzimidazol-1-yl)methyl]phenyl]-1-cyclopentene-1-carboxylate To a cooled (0° C.), stirred partial solution of 2-propyl-1H-benzimidazole (0.79 g, 4.96 mmol) in DMF (4 mL) was added NaH (60% dispersion in mineral oil; 0.20 g, 4.96 mmol). After 1.5 h, a solution of methyl [2-[(4-chloromethyl)phenyl]-1-cyclopentene]-1-carboxylate (1.13 g, 4.51 mmol) in DMF (1.5 mL) was added and the resultant mixture was stirred at room temperature for 18 h. Water was added and the mixture was extracted with EtOAc. The combined extracts were washed with brine, dried, and concentrated. Purification by flash chromatography (30% EtOAc/hexane) gave 1.63 g (96%) of product as a yellow oil.

$^1$H NMR (CDCl$_3$) δ 1.00 (t, J=7.5 Hz, 3H), 1.86 (m, 2H), 1.95 (m, 2H), 2.79 (m, 6H), 3.59 (s, 3H), 5.33 (s, 2H), 6.99 (d, J=8.2 Hz, 2H), 7.28 (m, 5H), 7.77 (d, J=7.5 Hz, 1H).

Step 5) 2-[4-[(2-Propyl-1H-benzimidazol-1-yl)methyl]phenyl]-1-cyclopentene-1-carboxylic Acid A mixture of methyl 2-[4-[(2-propyl-1H-benzimidazol-1-yl)methyl]phenyl]-1-cyclopentene-1-carboxylate (1.60 g, 4.27 mmol), 1N KOH (8.5 mL), and dioxane (8.5 mL) was heated under reflux for 1 h. The mixture was concentrated, diluted with water (10 mL), and extracted with ether (discarded). The aqueous phase was neutralized with 1N HCl (8.5 mL) and the white precipitate was collected by filtration. Trituration with EtOH gave 1.04 g (68%) of product, mp 224°–226° C.

$^1$H NMR (DMSO-d$_6$) δ 0.94 (t, J=7.3 Hz, 3H), 1.75 (m, 2H), 1.86 (m, 2H), 2.69 (t, J=7.5 Hz, 2H), 2.75 (t, J=7.5 Hz, 2H), 2.81 (t, J=7.5 Hz, 2H), 5.48 (s, 2H), 7.03 (d, J=8.3 Hz, 2H), 7.14 (m, 2H), 7.30 (d, J=8.3 Hz, 2H), 7.45 (m, 1H), 7.58 (m, 1H).

Anal. calcd for C$_{23}$H$_{24}$N$_2$O$_2$: C, 76.64; H, 6.71; N, 7.77 Found: C, 76.73; H, 6.90; N, 7.85.

EXAMPLE 4

2-[4-[(2-Propyl-1H-benzimidazol-1-yl)methyl]phenyl]-cyclopentane-1-carboxylic Acid Step 1) Methyl [2-[(4-Hydroxymethyl)phenyl]cyclopentane]-1-carboxylate To a solution of methyl [2-[(4-hydroxymethyl)phenyl]-1-cyclopentene]-1-carboxylate (0.85 g, 3.66 mmol), prepared as described in Step 2 of Example 3, in THF (5 mL) was added 0.1M SmI$_2$ in THF (91 mL, 9.1 mmol) and MeOH (176 mg, 5.49 mmol). After 3 days, 0.1N HCl (100 mL) was added and the mixture was extracted with ether. The combined extracts were washed with brine, dried, and concentrated to give an oil. $^1$H NMR analysis showed the oil to be a 1:2 mixture of starting material and product. The mixture was resubjected to the same reaction conditions as described above and worked up to give 785 mg (92%) of product as a white solid.

$^1$H NMR (CD$_3$CN) δ 1.60–2.20 (m, 6H), 2.80 (m, 1H), 3.20 (m, 1H), 3.53 (s, 3H), 4.51 (s, 2H), 7.23 (m, 4H).

Step 2) Methyl [2-[(4-Chloromethyl)phenyl]cyclopentane]-1-carboxylate

To a stirred, cooled (0° C.) solution of methyl [2-[(4-hydroxymethyl)phenyl]cyclopentane]-1-carboxylate (785 mg, 3.35 mmol), LiCl (185 mg, 4.36 mmol), and 2,6-lutidine (467 mg, 4.36 mmol) in DMF (6 mL) was added methanesulfonyl chloride (499 mg, 4.36 mmol). The cooling bath was removed and stirring was continued for 24 h. Water was added and the mixture was extracted with EtOAc. The combined extracts were washed with 1N HCl, brine, dried, and concentrated to give 760 mg (90%) of product as an oily solid.

$^1$H NMR (CD$_3$CN) δ 1.80–2.20 (m, 6H), 2.80 (m, 1H), 3.20 (m, 1H), 3.54 (s, 2H), 4.63 (s, 2H), 7.30 (m, 4H).

Step 3) Methyl 2-[4-[(2-Propyl-1H-benzimidazol-1-yl)methyl]phenyl]cyclopentane-1-carboxylate To a cooled (0° C.), stirred partial solution of 2-propyl-1H-benzimidazole (0.48 g, 3.00 mmol) in DMF (3 mL) was added NaH (60% dispersion in mineral oil; 0.12 g, 3.00 mmol). After 15 min, a solution of methyl [2-[(4-chloromethyl)phenyl]cyclopentane]-1-carboxylate (0.76 g, 3.00 mmol) in DMF (4 mL) was added and the resultant mixture was stirred at room temperature for 20 h. Water was added and the mixture was extracted with EtOAc. The combined extracts were washed with brine, dried, and concentrated. Purification by flash chromatography (30% EtOAc/hexane) gave 0.53 g (47%) of product as an oily solid.

$^1$H NMR (CDCl$_3$) δ 0.99 (t, J=7.3 Hz, 3H), 1.60–2.20 (m, 8H), 2.80 (m, 3H), 3.30 (m, 1H), 3.57 (s, 3H), 5.28 (s, 2H), 6.94 (d, J=8.3 Hz, 2H), 7.18 (m, 5H), 7.74 (d, J=7.3 Hz, 1H).

Step 4) 2-[4-[(2-Propyl-1H-benzimidazol-1-yl)methyl]phenyl]cyclopentane-1-carboxylic Acid A mixture of methyl 2-[4-[(2-propyl-1H-benzimidazol-1yl)methyl]phenyl]cyclopentane-1-carboxylate (530 mg, 1.41 mmol), 1N NaOH (2.8 mL), and MeOH (5.0 mL) was heated under reflux for 6 h. The mixture was concentrated, diluted with water (10 mL), and extracted with ether (discarded). The aqueous phase was neutralized with 1N HCl (2.8 mL) and the white precipitate was collected by filtration. Recrystallization from EtOH gave 320 mg (63%) of product, mp 179°–180° C.

$^1$H NMR (CDCl$_3$) δ 0.83 (t, J=7.2 Hz, 3H), 1.67 (m, 3H), 1.85 (m, 2H), 2.03 (m, 1H), 2.16 (m, 2H), 2.74 (t, J=7.6 Hz, 2H), 2.82 (m, 1H), 3.33 (q, J=7.7 Hz, 1H), 5.27 (s, 2H), 6.93 (d, J=8.1 Hz, 2H), 7.20 (m, 5H), 7.77 (d, J=6.8 Hz, 1H).

Anal. calcd for C$_{23}$H$_{26}$N$_2$O$_2$: C, 76.21; H, 7.23; N, 7.73 Found: C, 75.93; H, 7.26; N, 7.61.

EXAMPLE 5

2-Propyl-1-[2-[4-[2-(1H-tetrazol-5-yl)phenyl]-1-piperazinyl]ethyl]-1H-benzimidazole Potassium Salt Step 1) 2-[4-[(2-Hydroxyethyl)-1-piperazinyl]]benzonitrile A mixture of 1-(2-hydroxyethyl)piperazine (5.0 g, 0.038 mol), 2-fluorobenzonitrile (4.7 g, 0.038 mol), and potassium carbonate (5.3 g, 0.038 mol) in DMF (30 mL) was heated at 110° C. for 20 h. The mixture was cooled, filtered, and the filtrate was concentrated. Purification by flash chromatography (10% MeOH/CH$_2$Cl$_2$) gave 6.5 g (73%) of product as a brown solid, mp 70°–73° C.

$^1$H NMR (CDCl$_3$) δ 2.64 (t, J=5.4 Hz, 2H), 2.75 (t, J=5.0 Hz, 2H), 2.85 (s, 1H), 3.24 (t, J=5.0 Hz, 2H), 3.66 (t, J=5.4 Hz, 2H), 6.99 (m, 2H), 7.45 (m, 1H), 7.54 (dd, J=7.8, 1.6 Hz, 1H).

Step 2) [[4-(2-Cyanophenyl)-1-piperazinyl]ethyl]methanesulfonate

To a cooled solution of 2-[4-[(2-hydroxyethyl)-1-piperazinyl]]benzonitrile (2.00 g, 8.65 mmol) in CH$_2$Cl$_2$ (30 mL) was added methanesulfonyl chloride (1.20 g, 10.38 mmol). After 17 h, the solution was washed with saturated aqueous NaHCO$_3$, dried, and concentrated to give 2.7 g (100%) of product as a brown oil. This compound was used directly in the next reaction.

$^1$H NMR (CDCl$_3$) δ 2.80 (s, 3H), 3.22 (m, 6H), 3.44 (t, J=4.5 Hz, 4H), 3.86 (t, J=6.3 Hz, 2H), 7.08 (m, 2H), 7.54 (m, 2H).

Step 3) 2-Propyl-1-[2-[4-(2-cyanophenyl)-1-piperazinyl]ethyl]-1H-benzimidazole

To a solution of 2-propyl-1H-benzimidazole (1.4 g, 8.73 mmol) in DMF (9 mL) was added NaH (60% dispersion in mineral oil; 0.35 g, 8.73 mmol). After 30 min, the mixture was added to a solution of [[4-(2-cyanophenyl)-1-piperazinyl]ethyl]methanesulfonate (2.7 g, 8.73 mmol) in DMF (3 mL) and stirring was continued for 2 days. Water was added and the mixture was extracted with EtOAc. The extracts were washed with water, dried, and concentrated. Purification by flash chromatography (2% MeOH/CH$_2$Cl$_2$) gave 600 mg (18%) of product as a yellow oil.

$^1$H NMR (CDCl$_3$) δ 1.06 (t, J=7.5 Hz, 3H), 1.92 (m, 2H), 2.75 (m, 6H), 2.85 (t, J=4.4 Hz, 2H), 3.19 (m, 4H), 4.24 (t, J=6.9 Hz, 2H), 6.99 (m, 2H), 7.23 (m, 2H), 7.46 (m, 1H), 7.53 (d, J=7.6 Hz, 1H), 7.70 (d, J=8.4 Hz, 1H).

Step 4) 2-Propyl-1-[2-[4-[2-(1H-tetrazol-5-yl)phenyl]-1-piperazinyl]ethyl]-1H-benzimidazole Potassium Salt A mixture of 2-propyl-1-[2-[4-(2-cyanophenyl)- 1-piperazinyl]ethyl]-1H-benzimidazole (600 mg, 1.61 mmol), NaN$_3$ (105 mg, 1.61 mmol), and tri-n-butyltin chloride (523 mg, 1.61 mmol) in xylenes (10 mL) was heated under reflux for 68 h. The mixture was cooled and 1N HCl (10 mL) was added. The layers were separated, and the aqueous phase was extracted with EtOAc (discarded) and made basic with 1N NaOH (12 mL). The aqueous phase was extracted with CH$_2$Cl$_2$ (discarded) and the pH was adjusted to about 6 with 1N HCl (1 mL). The precipitate was collected by filtration and recrystallized from EtOH to give 243 mg (36%) of product as beige crystals, mp 232°-233° C.

$^1$H NMR (DMSO-d$_6$) δ 1.00 (t, J=7.5 Hz, 3H), 1.84 (m, 2H), 2.50 (m, 4H), 2.64 (t, J=6.6 Hz, 2H), 2.71 (m, 4H), 2.84 (t, J=7.3 Hz, 2H), 4.26 (t, J=6.6 Hz, 2H), 7.10-7.26 (m, 4H), 7.46-7.54 (m, 3H), 7.62 (dd, J=7.7, 1.7 Hz, 1H).

Anal. calcd for C$_{23}$H$_{28}$N$_8$.0.25H$_2$O: C, 65.61; H, 6.82; N, 26.61 Found: C, 65.62; H, 6.83; N, 26.57.

A potassium salt was made from 200 mg (0.48 mmol) of the above product and 1N KOH (460 μL, 0.46 mmol) in water (5 mL). Filtration and concentration gave 209 mg of product as a foam, mp >300° C.

EXAMPLE 6

2-Propyl-1-[2-[1-[2-(1H-tetrazol-5-yl)phenyl]-4-piperidinyl]ethyl]-1H-benzimidazole The title compound was prepared from 4-(2-hydroxyethyl)piperidine, by the procedure described in Example 5. The product was obtained as a white solid, mp 231°-233° C.

$^1$H NMR (DMSO-d$_6$) δ 1.00 (t, J=7.3 Hz, 3H), 1.38 (m, 2H), 1.71 (m, 4H), 1.85 (m, 2H), 2.58 (t, J=10.8 Hz, 2H), 2.81 (t, J=7.5 Hz, 2H), 2.87 (d, J=11.1 Hz, 2H), 4.19 (t, J=7.4 Hz, 2H), 7.08 (m, 3H), 7.26 (d, J=7.8 Hz, 1H), 7.50 (m, 3H), 7.65 (dd, J=7.5, 1.2 Hz, 1H).

Anal. calcd for C$_{24}$H$_{29}$N$_7$: C, 69.37; H, 7.03; N, 23.60 Found: C, 69.14; H, 7.09; N, 23.21.

EXAMPLE 7

2-Propyl-1-[[2-[2-(1H-tetrazol-5-yl)phenyl]-5-pyridinyl]methyl]-1H-benzimidazole Step 1) 2-Bromo-5-hydroxymethylpyridine To a cooled (0° C.), stirred suspension of 6-bromonicotinic acid (13.8 g, 0.068 mol), prepared according to Campbell, et al. *Aust. J. Chem.* 1971, 24,277, in THF (20 mL) was added 1.0M BH$_3$ in THF (204 mL, 0.204 mol). The mixture was stirred at room temperature for 3 h, recooled to 0° C., and saturated aqueous K$_2$CO$_3$ and water were added. The mixture was extracted with EtOAc, and the combined extracts were washed with water, dried, and concentrated to give a yellow oil. Purification by flash chromatography (2% MeOH/CH$_2$Cl$_2$) gave 7.5 g (59%) of a yellow solid, mp 49°-51° C.

$^1$H NMR (DMSO-d$_6$) δ 4.50 (d, J=5.7 Hz, 2H), 5.40 (t, J=5.7 Hz, 1H), 7.57 (d, J=8.3 Hz, 1H), 7.70 (dd, J=8.3, 1.5 Hz, 1H), 8.35 (d, J=1.5 Hz, 1H).

Step 2) 2-Bromo-5-(tert-butyldimethylsilyloxymethyl)pyridine

To a stirred mixture of 2-bromo-5-hydroxymethylpyridine (4.7 g, 0.023 mol) and triethylamine (3.4 mL, 0.024 mol) in DMF (30 mL) was added tertbutyldimethylsilyl chloride. After 1 h, the mixture was diluted with ether and washed with water. The ether phase was dried and concentrated to give 6.8 g (97%) of product as a colorless oil.

$^1$H NMR (DMSO-d$_6$) δ 0.10 (s, 6H), 0.90 (s, 3H), 4.73 (s, 2H), 7.65 (m, 2H), 8.35 (d, J=1.5 Hz, 1H).

Step 3) [5-(tert-Butyldimethylsilyloxymethyl)pyridin-2-yl]tri-n-butylstannane

To a cooled (−78° C.), stirred solution of 2-bromo-5-(tertbutyldimethylsilyloxy)methylpyridine (6.8 g, 0.022 mol) in THF (60 mL) was added 1.6M nBuLi in hexanes (14.1 mL, 0.022 mol). After 1 h, tri-n-butyltin chloride (6.1 mL, 0.022 mol) was added and stirring was continued for 3 h. Water was added, and the mixture was warmed to room temperature and extracted with ether. The combined extracts were dried and concentrated to give 11.5 g (100%) of product as a brown oil.

$^1$H NMR (DMSO-d$_6$) δ 0.10 (s, 6H), 0.80 (m, 18H), 1.10 (m, 6H), 1.25 (m, 6H), 1.50 (m, 6H), 4.73 (s, 2H), 7.55 (m, 2H), 8.61 (d, J=2.2 Hz, 1H).

Step 4) 2-[5-(tert-Butyldimethylsilyloxymethyl)pyridin-2-yl]benzonitrile

A mixture of [5-(tert-butyldimethylsilyloxymethyl)-pyridin-2-yl]tri-n-butylstannane (11.5 g, 0.022 mol), 2-iodobenzonitrile (5.1 g, 0.022 mol), CuI (0.43 g, 0.002 mol), and bis(triphenylphosphine)palladium(II) chloride (0.80 g, 0,001 mol) in THF (40 mL) was heated under reflux for 48 h. The mixture was diluted with ether and washed with saturated aqueous NH$_4$Cl, aqueous NH$_4$OH, water, and brine, dried, and concentrated to give 4.9 g (67%) of product as a brown oil.

$^1$H NMR (DMSO-d$_6$) δ 0.10 (s, 6H), 0.90 (s, 9H), 4.73 (s, 2H), 7.45 (m, 1H), 7.60 (m, 4H), 7.75 (dd, J=7.9, 2.2 Hz, 1H), 8.50 (d, J=2.2 Hz, 1H).

Step 5) 2-[5-(Hydroxymethyl)pyridin-2-yl]benzonitrile

A mixture of 2-[5-(tert-butyldimethylsilyloxymethyl)pyridin-2-yl]benzonitrile (4.9 g, 0.021 mol) and nBu$_4$NF hydrate (8.1 g, 0.031 mol) in THF (60 mL) was stirred at room temperature for 18 h. The mixture was diluted with EtOAc, washed with water and brine, dried, and concentrated to give 3.5 g (80%) of product as a brown solid, mp 152°-153° C.

$^1$H NMR (DMSO-d$_6$) δ 4.61 (d, J=5.6 Hz, 2H), 5.42 (t, J=5.6 Hz, 1H), 7.57 (dd, J=7.3, 1.5 Hz, 1H), 7.65 (m, 4H), 7.80 (dd, J=7.9, 2.2 Hz, 1H), 8.52 (d, J=2.2 Hz, 1H).

Step 6) 2-[5-(Chloromethyl)pyridin-2-yl]benzonitrile

To a cooled (0° C.), stirred solution of 2-[5-(hydroxymethyl)pyridin-2-yl]benzonitrile (4.3 g, 0.020 mol) and ZnCl$_2$ (0.09 g, 0.61 mmol) in p-dioxane (40 mL) was added thionyl chloride (1.50 mL, 0.020 mol) dropwise. The mixture was stirred at room temperature for 18 h, diluted with ether, washed with water and brine, dried, and concentrated to give 4.30 g (92%) of product as a brown solid, mp 97°-98° C.

$^1$H NMR (DMSO-d$_6$) δ 4.90 (s, 2H), 7.63 (dd, J=7.7, 1.3 Hz, 1H), 7.80 (m, 1H), 7.85 (m, 2H), 7.95 (d, J=7.7

Hz, 1H), 8.01 (dd, J=8.0, 2.2 Hz, 1H), 8.80 (d, J=2.2 Hz, 1H).

Step 7) 2-Propyl-1-[[2-(2-cyanophenyl)-5-pyridinyl]methyl]-1H-benzimidazole

To a cooled (0° C.), stirred partial solution of 2-propyl-1H-benzimidazole (0.31 g, 1.92 mmol) in THF (2 mL) was added NaH (60% dispersion in mineral oil; 0.08 g, 1.92 mmol). After 0.5 h, a solution of 2-[5-(chloromethyl)pyridin-2-yl]benzonitrile (0.48 g, 1.75 mmol) in THF (1.5 mL) was added and the resultant mixture was stirred at room temperature for 2 h. Water was added and the mixture was extracted with EtOAc. The combined extracts were washed with brine, dried, and concentrated. Purification by flash chromatography (2% MeOH/CH$_2$Cl$_2$) gave 0.54 g (87%) of product as a white solid, mp 84°-85° C.

$^1$H NMR (DMSO-d$_6$) δ 0.93 (t, J=7.3 Hz, 3H), 1.78 (m, 2H), 2.79 (t, J=7.3 Hz, 2H), 5.63 (s, 2H), 7.16 (m, 2H), 7.60 (m, 4H), 7.80 (m, 3H), 7.93 (dd, J=8.3, 2.3 Hz, 1H), 8.60 (d, J=1.6 Hz, 1H).

Step 8) 2-Propyl-1-[[2-[2-(1H-tetrazol-5-yl)phenyl]-5-pyridinyl]methyl]-1H-benzimidazole A mixture of 2-propyl-1-[[2-(2-cyanophenyl)-5-pyridinyl]methyl]-1H-benzimidazole (0.50 g, 1.42 mmol), NaN$_3$ (0.18 g, 2.84 mmol), and tri-n-butyltin chloride (0.92 g, 2.84 mmol) in xylenes (10 mL) was heated under reflux for 48 h. The reaction mixture was concentrated and 2N HCl was added. The mixture was extracted with ether (discarded) and adjusted to pH 5 with 50% NaOH. The aqueous phase was extracted with CH$_2$Cl$_2$, and the extracts were washed with water, dried, and concentrated. Purification by flash chromatography (5% MeOH/CH$_2$Cl$_2$) and trituration with EtOH gave 0.29 g (51%) of product as a white solid, mp 240°-241° C.

$^1$H NMR (DMSO-d$_6$) δ 0.93 (t, J=7.3 Hz, 3H), 1.74 (m, 2H), 2.82 (t, J=7.3 Hz, 2H), 5.53 (s, 2H), 7.16 (m, 2H), 7.35 (d, J=8.0 Hz, 1H), 7.41 (dd, J=8.3, 2.3 Hz, 1H), 7.52 (m, 1H), 7.65 (m, 5H), 8.27 (d, J=1.6 Hz, 1H).

Anal. calcd for C$_{23}$H$_{21}$N$_7$: C, 69.85; H, 5.35; N, 24.70 Found: C, 69.69; H, 5.38; N, 24.41.

EXAMPLE 8

4-Methyl-2-propyl-1-[[2-[2-(1H-tetrazol-5-yl)phenyl]-5-pyridinyl]methyl]-1H-benzimidazole Step 1 ) 4-Methyl-2-propyl-1-[[2-(2-cyanophenyl)-5-pyridinyl]methyl]-1H-benzimidazole To a cooled (0° C.), stirred suspension of NaH (60% dispersion in mineral oil; 0.21 g, 5.27 mmol) in DMF (10 mL) was added 4-methyl-2-propyl-1H-benzimidazole (0.76 g, 1.92 mmol). After 1 h, 2-[5-(bromomethyl)pyridin-2-yl]benzonitrile (0.48 g, 1.75 mmol) (prepared from 2-[5-(hydroxymethyl)pyridin-2-yl]benzonitrile of Step 5 in Example 7, triphenylphosphine, and carbon tetrabromide) was added and the resultant mixture was stirred at room temperature for 2 h. Water was added and the mixture was extracted with EtOAc. The combined extracts were washed with brine, dried, and concentrated. Purification by flash chromatography (2% MeOH/CH$_2$Cl$_2$) gave 0.87 g (54%) of product as an off-white solid, mp 129°-130° C.

$^1$H NMR (DMSO-d$_6$) δ 0.93 (t, J=7.3 Hz, 3H), 1.78 (m, 2H), 2.59 (s, 3H), 2.89 (t, J=7.3 Hz, 2H), 5.60 (s, 2H), 6.95 (d, J=7.3 Hz, 1H), 7.07 (m, 1H), 7.30 (d, J=7.3 Hz, 1H), 7.57 (m, 2H), 7.80 (m, 3H), 7.92 (m, 2H), 8.58 (d, J=1.4 Hz, 1H).

Step 2) 4-Methyl-2-propyl-1-[[2-[2-(1H-tetrazol-5-yl)phenyl]-5-pyridinyl]methyl]-1H-benzimidazole A mixture of 4-methyl-2-propyl-1-[[2-(2-cyanophenyl)-5-pyridinyl]methyl]-1H-benzimidazole (0.87 g, 2.39 mmol), NaN3 (0.77 g, 11.94 mmol), and tri-n-butyltin chloride (3.88 g, 11.94 mmol) in xylenes (20 mL) was heated under reflux for 20 h. The reaction mixture was concentrated and 2N HCl was added. The mixture was extracted with ether (discarded) and adjusted to pH 5 with 50% NaOH. The aqueous phase was extracted with CH$_2$Cl$_2$, and the extracts were washed with water, dried, and concentrated. Purification by flash chromatography (5% MeOH/CH$_2$Cl$_2$) and recrystallization from EtOH/EtOAc/ether gave 0.45 g (45%) of product as a white solid, mp 169°-170° C.

$^1$H NMR (DMSO-d$_6$) δ 0.93 (t, J=7.3 Hz, 3H), 1.70 (m, 2H), 2.50 (s, 3H), 2.81 (t, J=7.3 Hz, 2H), 5.51 (s, 2H), 6.96 (d, J=7.3 Hz, 1H), 7.05 (t, J=7.3 Hz, 1H), 7.37 (m, 3H), 7.65 (m, 6H), 8.18 (d, J=1.4 Hz, 1H).

Anal. calcd for C$_{24}$H$_{23}$N$_7$: C, 70.39; H, 5.66; N, 23.94 Found: C, 70.63; H, 5.88; N, 23.59.

EXAMPLE 9

5,6,7,8-Tetrahydro-N-I[2'-(1H-tetrazol-5-yl)phenyl]-5-pyridinyl]methyl]-2-(trifluoromethyl)-4-quinazolinamine Step 1 ) 2-[5-(Aminomethyl)pyridin-2-yl]benzonitrile Hydrobromide A solution of 2-[5-(bromomethyl)pyridin-2-yl]benzonitrile (1.00 g, 3.66 mmol) (prepared from 2-[5-(hydroxymethyl)pyridin-2-yl]benzonitrile of Step 5 in Example 7, triphenylphosphine, and carbon tetrabromide) in saturated ethanolic ammonia (20 mL) was stirred for 18 h. The mixture was concentrated and the residue was triturated with EtOH to give 0.74 g (70%) of product as a brown solid, mp 190°-192° C.

$^1$H NMR (DMSO-d$_6$) δ 4.20 (s, 2H), 7.62 (m, 1H), 7.90 (m, 4H), 8.10 (dd, J=8.3, 2.3 Hz, 1H), 8.30 (s, 3H), 8.80 (s, 1H).

Step 2) 5,6,7,8-Tetrahydro-2-trifluoromethyl-4-quinazolone

To a solution of NaOEt in EtOH (10 mL), prepared from Na (0.15 g, 6.5 mmol), was added 2-carboethoxycyclohexanone (1.00 g, 5.88 mmol) and 85% trifluoroacetamidine (0.78 g, 5.91 mmol). The mixture was heated under reflux for 18 h, and concentrated. The pH of the residue was adjusted to 6 with dilute HCl and the resulting solid was collected by filtration to give 0.73 g (57%) of product.

$^1$H NMR (DMSO-d$_6$) δ 1.78 (m, 4H), 2.45 (m, 2H), 2.78 (m, 2H), 13.00 (s, 1H).

Step 2) 4-Chloro-5,6,7,8-tetrahydro-2-trifluoromethylquinazoline

To a mixture of phosphorus oxychloride (6.0 mL) and N,N-dimethylaniline (1.0 mL) in toluene (20 mL) was added 5,6,7,8-tetrahydro-2-trifluoromethyl-4-quinazolone (3.00 g, 13.75 mmol). The resulting mixture was heated under reflux for 3 h and then cooled to room temperature. The reaction mixture was poured into an ice cold mixture of ether and water. The organic layer was separated, washed with brine, dried, and concentrated to yield 3.46 g of product as a brown solid.

Step 3) 5,6,7,8-Tetrahydro-N-[(2'-cyanophenyl)-5-pyridinyl]methyl]-2-(trifluoromethyl)-4-quinazolinamine A mixture of 4-chloro-5,6,7,8-tetrahydro-2-trifluoromethylquinazoline (0.60 g, 2.54 mmol), 2-[5-

(aminomethyl)pyridin-2-yl]benzonitrile hydrobromide (0.74 g, 2.54 mmol), iPr₂NEt (0.65 g, 5.07 mmol), and nBuOH (20 mL) was heated under reflux for 2 days. The mixture was concentrated, taken up in water, and extracted with CH₂Cl₂. The combined extracts were dried and concentrated. Purification by flash chromatography (1% MeOH/CH₂Cl₂) gave 0.25 g (24%) of product as a yellow foam.

¹H NMR (DMSO-d₆) δ 1.50–1.70 (m, 4H), 2.42 (s, 2H), 2.63 (s, 2H), 4.70 (d, J=5.8 Hz, 2H), 7.65 (m, 1H), 7.82 (m, 6H), 8.75 (s, 1H).

Step 4) 5,6,7,8-Tetrahydro-N-[[2'-(1H-tetrazol-5-yl)phenyl]-5-pyridinyl]methyl]-2-(trifluoromethyl)-4-quinazolinamine A mixture of 5,6,7,8-tetrahydro-N-[(2'-cyanophenyl)-5-pyridinyl]methyl]-2-(trifluoromethyl)-4-quinazolinamine (0.25 g, 0.61 mmol), NaN₃ (0.20 g, 3.05 mmol), and tri-n-butyltin chloride (0.99 g, 3.05 mmol) in xylenes (5 mL) was heated under reflux for 3 days. The reaction mixture was concentrated and 2N HCl was added. The mixture was extracted with ether (discarded) and adjusted to pH 5 with 50% NaOH. The aqueous phase was extracted with CH₂Cl₂, and the extracts were washed with water, dried, and concentrated. Purification by flash chromatography (5% MeOH/CH₂Cl₂) and trituration with ether/CH₂Cl₂ gave 0.09 g (33%) of product as a white solid, mp 188°–189° C.

¹H NMR (DMSO-d₆) δ 1.73 (m, 4H), 2.40 (t, J=7.3 Hz, 2H), 2.60 (t, J=7.3 Hz, 2H), 4.60 (d, J=5.8 Hz, 2H), 7.35 (d, J=8.1 Hz, 1H), 7.65 (m, 5H), 7.83 (m, 1H), 8.38 (s, 1H).

Anal. calcd for C₂₂H₁₉F₃N₈·0.5H₂O: C, 57.26; H, 4.37; N, 24.27 Found: C, 56.96; H, 4.29; N, 24.52.

EXAMPLE 10

2-[4-[(2-Propyl-1H-benzimidazol-1-yl)methyl]phenyl]-3-pyridinecarboxylic Acid

Step 1) Methyl 2-[(4-Hydroxymethyl)phenyl]-3-pyridinecarboxylate

To a stirred solution of methyl 2-bromo-3-pyridinecarboxylate (3.45 g, 14.39 mmol) and 4-(trimethylstannyl)benzyl alcohol (3.90 g, 14.39 mmol), prepared as described in Step 1 of Example 3, in DMF (25 mL) was added bis(acetonitrile)palladium dichloride (0.19 g, 0.72 mmol) and CuI (0.27 g, 1.44 mmol). After 18 h, bis(triphenylphosphine)palladium dichloride (0.20 g, 0.28 mmol) and CuI (0.11 g, 0.57 mmol) were added and stirring was continued for 2 days at room temperature. The mixture was concentrated, taken up in water, and extracted with EtOAc. The combined extracts were washed with brine, dried, and concentrated. Purification by flash chromatography (50% EtOAc/hexane) gave 277 mg (8%) of product as a yellow oil.

¹H NMR (CDCl₃) δ 3.69 (s, 3H), 4.69 (s, 2H), 7.35 (m, 1H), 7.38 (d, J=8.2 Hz, 2H), 7.49 (d, J=8.2 Hz, 2H), 8.08 (dd, J=7.9, 1.8Hz, 1H), 8.75 (m, 1H).

Step 2) Methyl 2-[(4-Chloromethyl)phenyl]-3-pyridinecarboxylate

To a solution of methyl 2-[(4-hydroxymethyl)phenyl]-3-pyridinecarboxylate (277 mg, 1.14 mmol) and ZnCl₂ (5 mg, 0.03 mmol) in dioxane (4 mL) was added thionyl chloride (542 mg, 4.56 mmol). After 3 h, the mixture was concentrated and purified by flash chromatography (20% EtOAc/hexane) to give 100 mg (33%) of product as a yellow oil.

¹H NMR (CDCl₃₁) δ 3.69 (s, 3H), 4.62 (s, 2H), 7.32 (dd, J=7.8, 4.8 Hz, 1H), 7.44 (d, J=8.3 Hz, 2H), 7.53 (d, J=8.3 Hz, 2H), 8.09 (dd, J=7.8, 1.8 Hz, 1H), 8.75 (dd, J=4.8, 1.8 Hz, 1H).

Step 3) Methyl 2-[4-[(2-Propyl-1H-benzimidazol-1-yl)methyl]phenyl]-3-pyridinecarboxylate To a solution of 2-propyl-1H-benzimidazole (57 mg, 0.42 mmol) in DMF (1.5 mL) was added NaH (50% dispersion in mineral oil; 17 mg, 0.42 mmol). After 20 min, a solution of methyl 2-[(4-chloromethyl)phenyl]-3-pyridinecarboxylate (100 mg, 0.38 mmol) in DMF (3 mL) was added. After 20 h, the mixture was cooled (0° C.) and water (10 mL) and brine (5 mL) were added. The mixture was extracted with EtOAc, and the combined extracts were washed with brine, dried, and concentrated. Purification by flash chromatography (30% EtOAc/hexane) gave 138 mg (94%) of product as a colorless oil.

¹H NMR (CDCl₃₁) δ 0.96 (t, J=7.3 Hz, 3H), 1.81 (m, 2H), 2.77 (t, J=7.9 Hz, 2H) 3.61 (s, 3H), 5.32 (s, 2H), 7.05 (d, J=8.3 Hz, 2H), 7.14 (m, 3H), 7.26 (dd, J=7.8, 4.8 Hz, 1H), 7.42 (d, J=8.3 Hz, 2H), 7.71 (d, J=7.6 Hz, 1H), 8.03 (dd, J=7.8, 1.8 Hz, 1H), 8.68 (dd, J=4.8, 1.8 Hz, 1H).

Step 4) 2-[4-[(2-Propyl-1H-benzimidazol-1-yl)methyl]phenyl]-3-pyridinecarboxylic Acid A mixture of methyl 2-[4-[(2-propyl-1H-benzimidazol-1-yl)methyl]phenyl]-3-pyridinecarboxylate (138 mg, 0.36 mmol), 1N NaOH (72 μL, 0.72 mmol), and dioxane (4 mL) was heated at 80° C. for 2 h. The mixture was concentrated and 0.1N HCl (7.2 mL) was added. The mixture was extracted with EtOAc, and the extracts were dried and concentrated to give 36 mg (27%) of product as a white solid, mp 238°–239° C.

¹H NMR (DMSO-d₆) δ 0.94 (t, J=7.3 Hz, 3H), 1.76 (m, 2H), 2.82 (t, J=7.5 Hz, 2H), 5.55 (s, 2H), 7.14 (m, 4H), 7.48 (m, 4H), 7.58 (m, 1H), 8.06 (dd, J=7.8, 1.5 Hz, 1H), 8.70 (dd, J=4.7, 1.5 Hz, 1H).

Anal. calcd for C₂₃H₂₁N₃O₂·0.25H₂O: C, 73.48; H, 5.76; N, 11.18 Found: C, 73.70; H, 5.74; N, 11.02.

What is claimed is:

1. A compound having the formula

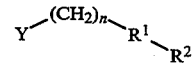

wherein
R¹ is

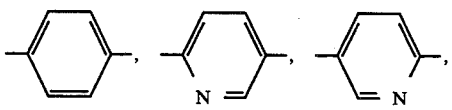

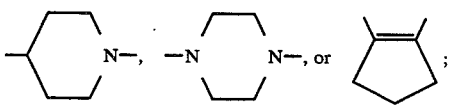

R² is

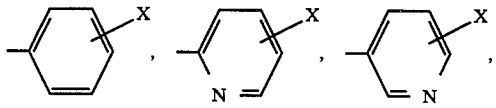

-continued

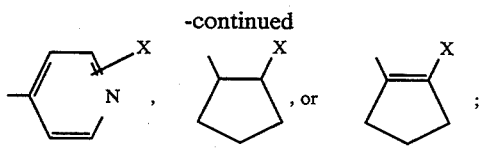

wherein X is

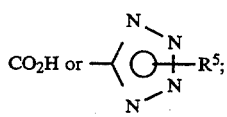

wherein R⁵ is hydrogen, alkyl of 1-6 carbon atoms, benzyl, triphenylmethyl, or Sn(alkyl of 1-6 carbon atoms)₃;
n is 1 to 3;
Y is

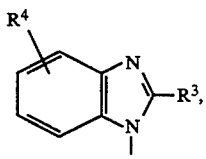

wherein R³ is hydrogen, perfluoro alkyl of 1-6 carbon atoms, trifluoro-methylalkyl of 1-6 carbon atoms, or alkyl of 1-6 carbon atoms; and R⁴ is hydrogen or alkyl of 1-6 carbon atoms;
with the proviso that when R¹ is

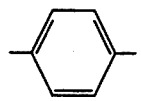

then R² cannot be

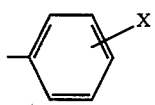

wherein X is as defined above;
and the pharmaceutically acceptable salts thereof.

2. The compound according to claim 1 having the formula

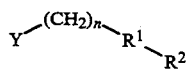

wherein
R¹ is

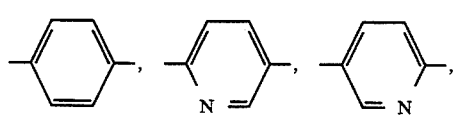

-continued

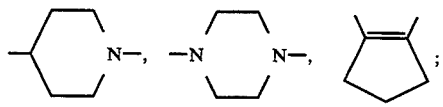

R² is

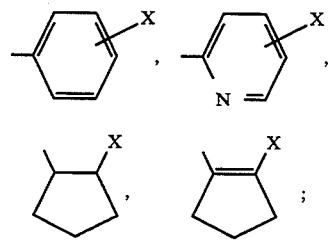

wherein X is

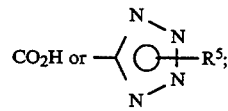

wherein R⁵ is hydrogen, alkyl of 1-6 carbon atoms, benzyl, triphenylmethyl, or. Sn(alkyl of 1-6 carbon atoms)₃;
n is 1 to 3;
Y is

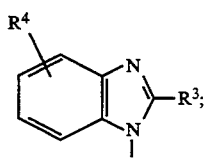

wherein R³ is hydrogen, perfluoro alkyl of 1-6 carbon atoms, trifluoromethylalkyl of 1-6 carbon atoms, or alkyl of 1-6 carbon atoms; and R⁴ is hydrogen or alkyl of 1-6 carbon atoms;
with the proviso that when R¹ is

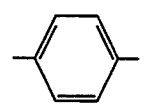

then R² cannot be

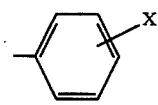

wherein X is as defined above;
and the pharmaceutically acceptable salts thereof.

3. The compound according to claim 2 2-propyl-1-[[2-[2-(1H-tetrazol-5-yl)phenyl]-1-cyclopentenyl]methyl]-1H-benzimidazole and the pharmaceutically acceptable salts thereof.

4. The compound according to claim 2 2-propyl-1-[[2-[3-(1H-tetrazol-5-yl)phenyl]-1-cyclopentenyl]methyl]-1H-benzimidazole and the pharmaceutically acceptable salts thereof.

5. The compound according to claim 2 2-[4-[(2-propyl-1H-benzimidazol-1-yl)methyl]phenyl]-1-cyclopentene-1-carboxylic acid and the pharmaceutically acceptable salts thereof.

6. The compound according to claim 2 2-[4-[(2-propyl-1H-benzimidazol-1-yl)methyl]phenyl]cyclopentane-1-carboxylic acid and the pharmaceutically acceptable salts thereof.

7. The compound according to claim 2 2-propyl-1-[2-[4-[2-(1H-tetrazol-5-yl)phenyl]-1-piperazinyl]ethyl]-1H-benzimidazole and the pharmaceutically acceptable salts thereof.

8. The compound according to claim 2 2-propyl-1-[2-[1-[2-(1H-tetrazol-5-yl)phenyl]-4-piperidinyl]ethyl]-1H-benzimidazole and the pharmaceutically acceptable salts thereof.

9. The compound according to claim 2 2-propyl-1-[[2-[2-(1H-tetrazol-5-yl)phenyl]-5-pyridinyl]methyl]-1H-benzimidazole and the pharmaceutically acceptable salts thereof.

10. The compound according to $C_1$ aim 2 4-methyl-2-propyl-I-[[2-[2-(1H-tetrazol-5-yl)phenyl]-5-pyridinyl]methyl]-1H-benzimidazole and the pharmaceutically acceptable salts thereof.

11. A method for preventing or treating restenosis following angioplasty in a mammal by administering to that mammal in an amount effective to prevent a narrowing or constriction of the diameter of the heart vessels following angioplasty a compound in claim 1.

12. The compound according to claim 2 2-[4-[(2-propyl-1H-benzimidazol-1-yl)methyl]phenyl]-3-pyridinecarboxylic acid and the pharmaceutically acceptable salts thereof.

13. A method of treating hypertension in a warm-blooded animal comprising administering to the animal a compound in claim 1 in an amount effective to lower the animal's blood pressure.

14. A method of treating congestive heart failure in a warm-blooded animal comprising administering to the animal a compound in claim 1 in an amount effective to correct the hemodynamic burden on the heart to relieve the congestion.

* * * * *